United States Patent
Wang et al.

(10) Patent No.: US 10,524,726 B2
(45) Date of Patent: Jan. 7, 2020

(54) MEDICATION ADHERENCE AND/OR COUNTERFEIT DETECTION WEARABLE ELECTRONIC DEVICE

(71) Applicant: BIOINTELLISENSE, INC., Redwood City, CA (US)

(72) Inventors: David Jonq Wang, Palo Alto, CA (US); Mark A. Ross, San Carlos, CA (US)

(73) Assignee: BIOINTELLISENSE, INC., Redwood City, CA (US)

( * ) Notice: Subject to any disclaimer, the term of this patent is extended or adjusted under 35 U.S.C. 154(b) by 0 days.

(21) Appl. No.: 15/353,738

(22) Filed: Nov. 17, 2016

(65) Prior Publication Data

US 2018/0132783 A1    May 17, 2018

(51) Int. Cl.
*A61B 5/00*    (2006.01)
*A61B 5/145*    (2006.01)
(Continued)

(52) U.S. Cl.
CPC ........ *A61B 5/4833* (2013.01); *A61B 5/14517* (2013.01); *A61B 5/14546* (2013.01); *A61B 5/4266* (2013.01); *A61B 5/681* (2013.01); *A61B 5/6803* (2013.01); *A61B 5/0402* (2013.01); *A61B 5/117* (2013.01); *A61B 5/1172* (2013.01); *A61B 5/1455* (2013.01)

(58) Field of Classification Search
CPC ..... A61B 5/4833; A61B 5/681; A61B 5/6803; A61B 5/4266; A61B 5/14546; A61B 5/14517; A61B 5/1455; A61B 5/1172; A61B 5/117; A61B 5/0402
See application file for complete search history.

(56) References Cited

U.S. PATENT DOCUMENTS

| | | | |
|---|---|---|---|
| 5,036,861 A | 8/1991 | Sembrowich et al. |
| 5,140,985 A | 8/1992 | Schroeder et al. |
(Continued)

FOREIGN PATENT DOCUMENTS

| | | |
|---|---|---|
| EP | 357309 A2 | 3/1990 |
| EP | 2682745 A1 | 1/2014 |
(Continued)

OTHER PUBLICATIONS

Gardner, J.W. et al., CMOS Interfacing for Integrated Gas Sensors: A Review, IEEE Sensors Journal, vol. 10, Issue 12, Dec. 2010, pp. 1833-1848.

(Continued)

*Primary Examiner* — Christian Jang
(74) *Attorney, Agent, or Firm* — Maschoff Brennan

(57) ABSTRACT

A system to determine medication adherence may include a chemical marker sensor, a verification sensor, and a processor. The chemical marker sensor may be configured to detect one or more markers in sweat vapor of a user. The verification sensor may be configured to detect whether the system is in use. The processor may be communicatively coupled to the chemical marker sensor and the verification sensor and may be configured to determine whether the user has taken a therapeutic agent that includes the one or more markers based on signals generated by the chemical marker sensor and the verification sensor.

12 Claims, 4 Drawing Sheets

(51) Int. Cl.
*A61B 5/0402* (2006.01)
*A61B 5/117* (2016.01)
*A61B 5/1172* (2016.01)
*A61B 5/1455* (2006.01)

(56) References Cited

U.S. PATENT DOCUMENTS

| | | | |
|---|---|---|---|
| 5,817,012 | A | 10/1998 | Schoendorfer |
| 6,269,265 | B1 | 7/2001 | Anderson |
| 6,981,947 | B2 | 1/2006 | Melker |
| 7,153,272 | B2 | 12/2006 | Talton |
| 7,820,108 | B2 | 10/2010 | Lampotang et al. |
| 8,273,021 | B2 | 9/2012 | Jang et al. |
| 8,285,356 | B2 | 10/2012 | Bly et al. |
| 8,872,663 | B2 | 10/2014 | Forster |
| 8,961,415 | B2 | 2/2015 | LeBoeuf et al. |
| 9,046,650 | B2 | 6/2015 | Lin et al. |
| 9,060,683 | B2 | 6/2015 | Tran |
| 9,075,910 | B2 | 7/2015 | Bhavaraju et al. |
| 9,326,713 | B2 | 5/2016 | Carroll |
| 9,357,946 | B2 | 6/2016 | Johnson |
| 2005/0123177 | A1 | 6/2005 | Abiko |
| 2005/0233459 | A1 | 10/2005 | Melker et al. |
| 2007/0224128 | A1* | 9/2007 | Dennis ................ A61B 5/4839 424/10.1 |
| 2007/0260174 | A1 | 11/2007 | Jung et al. |
| 2008/0059226 | A1 | 3/2008 | Melker et al. |
| 2010/0228567 | A1* | 9/2010 | Wulf ................ G06F 19/3456 705/3 |
| 2010/0255598 | A1 | 10/2010 | Melker et al. |
| 2011/0054273 | A1* | 3/2011 | Omoda ................ A61B 5/117 600/309 |
| 2012/0316406 | A1* | 12/2012 | Rahman ............... G01C 22/006 600/301 |
| 2012/0316897 | A1* | 12/2012 | Hanina ............... G06F 19/3456 705/3 |
| 2013/0231871 | A1 | 9/2013 | Hok et al. |
| 2013/0276785 | A1* | 10/2013 | Melker ............... A61M 5/1723 128/204.23 |
| 2014/0135594 | A1* | 5/2014 | Yuen .................. A61B 5/6885 600/301 |
| 2014/0153794 | A1* | 6/2014 | Varaklis ............... A61B 5/1124 382/128 |
| 2014/0257206 | A1* | 9/2014 | Fateh .................. A61F 9/0026 604/290 |
| 2014/0294675 | A1 | 10/2014 | Melker et al. |
| 2015/0112165 | A1 | 4/2015 | Heikenfeld |
| 2015/0127737 | A1 | 5/2015 | Thompson et al. |
| 2015/0138556 | A1 | 5/2015 | LeBoeuf et al. |
| 2015/0173674 | A1 | 6/2015 | Hayes et al. |
| 2015/0269825 | A1 | 9/2015 | Tran |
| 2015/0351690 | A1 | 12/2015 | Toth et al. |
| 2016/0073955 | A1 | 3/2016 | Salem |
| 2016/0095547 | A1 | 4/2016 | Wang et al. |
| 2016/0106935 | A1 | 4/2016 | Sezan et al. |
| 2016/0166203 | A1 | 6/2016 | Goldstein |
| 2016/0235309 | A1 | 8/2016 | Olivier |
| 2016/0278692 | A1 | 9/2016 | Larson et al. |
| 2016/0324442 | A1 | 11/2016 | Zdeblick |
| 2016/0328991 | A1 | 11/2016 | Simpson et al. |
| 2016/0331235 | A1 | 11/2016 | Nyberg |
| 2017/0095184 | A1* | 4/2017 | Heikenfeld ........ A61B 5/14517 |

FOREIGN PATENT DOCUMENTS

| | | |
|---|---|---|
| GB | 2535614 A | 8/2016 |
| WO | WO2001034024 A1 | 5/2001 |
| WO | WO2009107135 A2 | 9/2009 |
| WO | 2015/184084 A2 | 12/2015 |
| WO | WO2015184065 A1 | 12/2015 |
| WO | WO2016090189 A1 | 6/2016 |
| WO | 2016/153313 A1 | 9/2016 |

OTHER PUBLICATIONS

Kulkarni, G.S. et al., Graphene nanoelectronic heterodyne sensor for rapid and sensitive vapour detection, nature communications, DOI: 10.1038/ncomms5376, Jul. 7, 2014, 7 pgs.

Lee, H.J., et al., Highly Sensitive Detection of DMMP Using a CMUT-based Chemical Sensor, IEEE Sensors 2010 Conference, available at http://stanford.edu/group/khuri-yakub/publications/10_Lee_01.pdf (accessed on Nov. 15, 2016), pp. 2122-2126.

International Search Report dated Nov. 13, 2017 as received in Application No. PCT/US2017/051247.

Written Opinion of the International Searching Authority dated Nov. 13, 2017 as received in Application No. PCT/US2017/051247.

\* cited by examiner

MEDICATION ADHERENCE AND/OR COUNTERFEIT DETECTION WEARABLE ELECTRONIC DEVICE

FIELD

Some embodiments described herein generally relate to medication adherence and/or counterfeit detection wearable electronic devices.

BACKGROUND

Unless otherwise indicated herein, the materials described herein are not prior art to the claims in the present application and are not admitted to be prior art by inclusion in this section.

It is highly desirable to know whether someone taking medications is adhering to their prescription. Insurance companies and other risk-bearers may be particularly interested in ensuring that prescription medications are taken by the insured. Additionally, most medicine recommendations are based on "standards" rather than a metabolized amount of an active ingredient or ingredients. Some methods for determining medication adherence include self-reporting by the users that are taking medications. Self-reporting methods may be cumbersome to users and/or may be inaccurate.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Some example embodiments described herein generally relate to medication adherence and/or counterfeit detection wearable electronic devices. According to some embodiments, such wearable electronic devices may analyze perspiration in the form of sweat vapor of a user to determine concentration of one or more marker chemicals to determine whether the user has taken a therapeutic agent such as a medication. As used herein, "sweat vapor" is to be broadly construed to include one or more chemicals and/or chemical compounds emitted at or near a skin surface of a human or non-human (e.g., animal) being and transported there through sweat glands and/or eccrine glands of the skin.

In an example embodiment, a system to determine medication adherence may include a chemical marker sensor, a verification sensor, and a processor. The chemical marker sensor may be configured to detect one or more markers in sweat vapor of a user. The verification sensor may be configured to detect whether the system is in use. The processor may be communicatively coupled to the chemical marker sensor and the verification sensor and may be configured to determine whether the user has taken a therapeutic agent that includes the one or more markers based on signals generated by the chemical marker sensor and the verification sensor.

In another example embodiment, a method to determine medication adherence includes detecting whether a wearable electronic device is in use. The method also includes detecting one or more markers in sweat vapor of a user using a chemical marker sensor of the wearable electronic device. The method also includes, in response to detecting that the system is in use, determining whether the user has taken a therapeutic agent that includes the one or more markers based on detecting the one or more markers in the sweat vapor.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which.

DETAILED DESCRIPTION OF SOME EXAMPLE EMBODIMENTS

Figure 1:
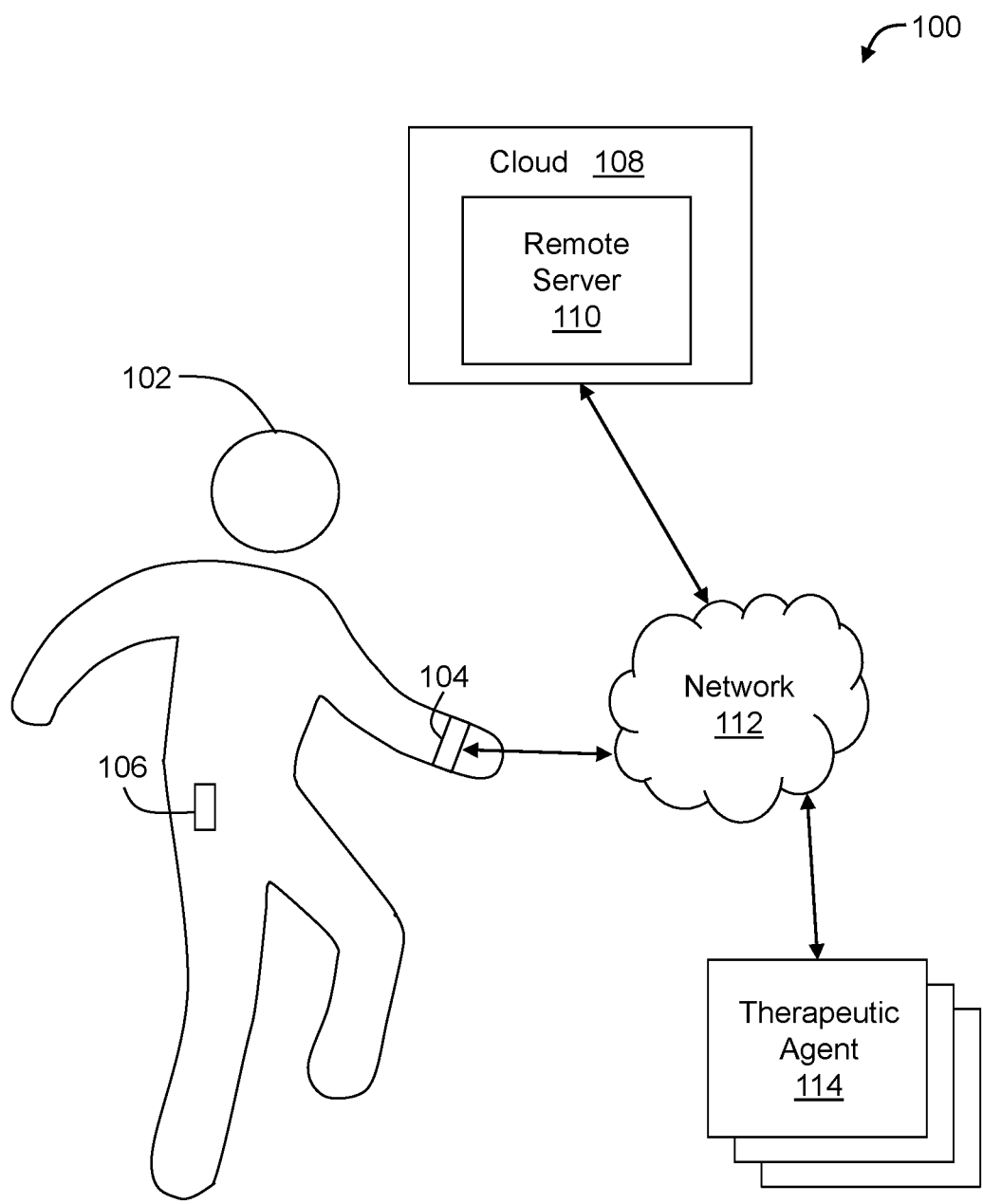
FIG. 1 illustrates an example environment in which some embodiments described herein can be implemented.

Some embodiments described herein generally relate to medication adherence and/or counterfeit detection wearable electronic devices. Such wearable electronic devices can be embodied as wrist-worn fitness trackers, smartwatches, clip-on ear rings or other ear accessories, hearing aids, dermal patches, armbands, a finger rings, smart watchbands, or other wearable electronic devices. Such wearable electronic devices may be configured to detect, e.g., medication adherence.

In particular, such wearable electronic devices may be configured to detect whether a user is taking prescribed medications, over the counter medications, or any other treatment substance, all of which may be generically referred to herein as therapeutic agents. The therapeutic agents may be embodied as and/or delivered in the form of pills, capsules, inhalers, consumable liquids, dermal patches, injections, slow-release implantables, or in any other suitable form. The therapeutic agents may each include one or more markers that may be excreted in sweat of the user.

Example markers include generally regarded as safe (GRAS) molecules which can be mixed together with one or more active ingredients of the therapeutic agent.

Various marker schemes can be used to identify therapeutic agents. For instance one or more of the therapeutic agents may each include a single unique marker that uniquely identifies the therapeutic agent. Alternatively or additionally, one or more of the therapeutic agents may each include a unique combination of two or more markers that uniquely identifies the therapeutic agent. Alternatively or additionally, one or more of the therapeutic agents may each include two or more markers in a unique combination and concentrations that together uniquely identifies the therapeutic agent.

In some embodiments, a given therapeutic agent may include multiple markers with different manifestation times. For instance, a first one of the markers may manifest, and thus be detectable, relatively quickly (e.g., immediately) after the therapeutic agent is taken by the user, while a second one of the markers may manifest relatively slowly (e.g., at a "normal" metabolic rate of the user) after the therapeutic agent is taken by the user. Using a combination of two such markers, embodiments described herein may determine a "diffusion equation" of the therapeutic agent for a given user, which may enable personalized dosing.

Each wearable electronic device may include a perspiration sensor to detect sweat vapor of a user, a chemical marker sensor to detect one or more markers in the sweat vapor, and a verification sensor to detect whether the wearable electronic device is in use, e.g., in contact with skin. After the user takes a therapeutic agent that includes one or more markers, the one or more markers may be excreted through the user's skin, e.g., through the user's sweat glands and/or eccrine glands and in the form of sweat vapor as defined above. The user's sweat vapor may include the one or more markers, identities and/or quantities of which may be detected in the sweat vapor by the chemical marker sensor. The chemical marker sensor may detect the one or more markers in the sweat vapor, as opposed to directly in the sweat, to avoid external contamination. The perspiration sensor may detect a quantity of the sweat vapor. A concentration of the one or more markers as a percentage of the sweat vapor may be determined based on the detected quantity of each of the one or more markers and the detected quantity of the sweat vapor. The perspiration sensor may be included in at least some embodiments in which the one or more markers include water-soluble marker chemicals. In other embodiments, the perspiration sensor may be omitted. For instance, the perspiration sensor may be omitted in embodiments in which the one or more markers include volatile organic compounds (VOCs).

Signals from the sensors may be used in combination to determine whether the user has taken the therapeutic agent. For instance, if the verification sensor indicates that the wearable electronic device is in use and the chemical marker sensor detects one or more markers in the sweat vapor, it may be determined that the user has taken the therapeutic agent that includes the one or more markers. Alternatively or additionally, the user wearing the wearable electronic device may be biometrically authenticated to confirm an identity of the user, e.g., as a particular known person with a prescription for the therapeutic agent. Such embodiments may be used to monitor and/or prevent prescription fraud where one person is prescribed a therapeutic agent and provides it to someone else for consumption.

In some embodiments, additional information and/or signals may be used to increase a confidence in the determination that the user has taken the therapeutic agent. For instance, the confidence in the determination may be increased based on subjective data, such as input from the user that indicates that the user has taken the therapeutic agent. Alternatively or additionally, such subjective data may include input from the user that indicates a self-assessment by the user of a condition being treated by the therapeutic agent, e.g., whether the condition is improving, which may indicate whether the user has taken the therapeutic agent. Alternatively or additionally, the confidence in the determination may be increased based on objective data such as objective measurements from an accelerometer, heart rate monitor, or other sensor. Such measurements may indicate whether an expected effect of the therapeutic agent is manifest in the user, which in turn may indicate whether the user has taken the therapeutic agent. Alternatively or additionally, the confidence in the determination may be increased based on calendar information indicative of any reminders related to the user taking the therapeutic agent, such as whether and/or when a reminder to take the therapeutic agent was given by the wearable electronic device to the user.

Information from at least the chemical sensor and the verification sensor, and optionally from the perspiration sensor and one or more other sources of subjective data, objective data, and/or calendar information may be processed locally at the wearable electronic device to determine whether the user has taken the therapeutic agent. Alternatively or additionally, some or all of the information may be communicated to a remote server, e.g., in the cloud, for remote processing to determine whether the user has taken the therapeutic agent. Multiple determinations of whether the user has taken the therapeutic agent may be made over time to validate medication adherence of the user.

Reference will now be made to the drawings to describe various aspects of some example embodiments of the disclosure. The drawings are diagrammatic and schematic representations of such example embodiments, and are not limiting of the present disclosure, nor are they necessarily drawn to scale.

FIG. 1 illustrates an example environment 100 in which some embodiments described herein can be implemented. The environment 100 includes a user 102 and a wearable electronic device 104. The environment 100 may additionally include a smartphone 106, a cloud computing environment (hereinafter "cloud 108") that includes at least one remote server 110, a network 112, one or multiple therapeutic agents 114, multiple third parties (not shown) and multiple wearable electronic devices (not shown) of the third parties.

The network 112 may include one or more wide area networks (WANs) and/or local area networks (LANs) that enable the wearable electronic device 104, the smartphone 106, the cloud 108, the remote server 110, and/or other wearable electronic devices to communicate with each other. In some embodiments, the network 112 includes the Internet, including a global internetwork formed by logical and physical connections between multiple WANs and/or LANs. Alternately or additionally, the network 112 may include one or more cellular RF networks and/or one or more wired and/or wireless networks such as, but not limited to, 802.xx networks, Bluetooth access points, wireless access points, IP-based networks, or the like. The network 112 may also include servers that enable one type of network to interface with another type of network.

The environment 100 additionally includes multiple sensors. As described in more detail below, the sensors may include at least a chemical marker sensor and a verification sensor. Alternatively or additionally, the sensors may include a perspiration sensor to detect sweat vapor, a biometric authentication sensor to biometrically authenticate the user and/or one or more other sensors from which it may be determined whether an expected effect of the therapeutic agent is manifest in the user. For instance, the biometric authentication sensor may include at least one of an accelerometer to determine user-specific gait characteristics, a fingerprint scanner to determine user-specific fingerprint characteristics, a microphone to determine user-specific voice characteristics, a camera or other image sensor to detect user-specific image characteristics (e.g., facial characteristics), or an electrocardiogram (ECG) or photoplethysmograph (PPG) sensor to detect user-specific heart beat characteristics. As another example, the one or more other sensors may include at least one of an accelerometer, a gyroscopic sensor, an ECG sensor, or a PPG sensor to detect manifestations of the expected effect of the therapeutic agent in the user.

All of the sensors may be included in a single device, such as the wearable electronic device 104 or the smartphone 106. Alternately or additionally, the sensors may be distributed between two or more devices. For instance, one or both of the wearable electronic device 104 or the smartphone 106 may include a sensor. Alternatively or additionally, one or more of the sensors may be provided as separate discrete sensors that are separate from either of the wearable electronic device 104 or the smartphone 106. According to some embodiments, the wearable electronic device 104 or the smartphone 106 may serve as a hub that receives data from the other and/or from discrete sensors and processes the data and/or transmits the data to the cloud 108 for processing. Thus, one or both of the wearable electronic device 104 or the smartphone 106 may include a suitable network connection (e.g., cellular or WAN connection) to send data to and/or receive data from the cloud 108. Alternatively or additionally, the environment 100 may further include a personal computer (PC) dongle, an internet of things (TOT) appliance or other device that receives data from and/or sends data to the wearable electronic device 104 over a relatively limited network connection like Bluetooth and can then transmit data to and/or receive data from the cloud 108 using a cellular connection, WAN connection, or other suitable connection.

The wearable electronic device 104 may be embodied as a portable electronic device and may be borne by the user 102 throughout the day and/or at other times and with one or more of its sensors (e.g., the chemical marker sensor and/or the verification sensor) in contact or near contact with the skin at any of a variety of locations on the body of the user 102.

Figure 2:
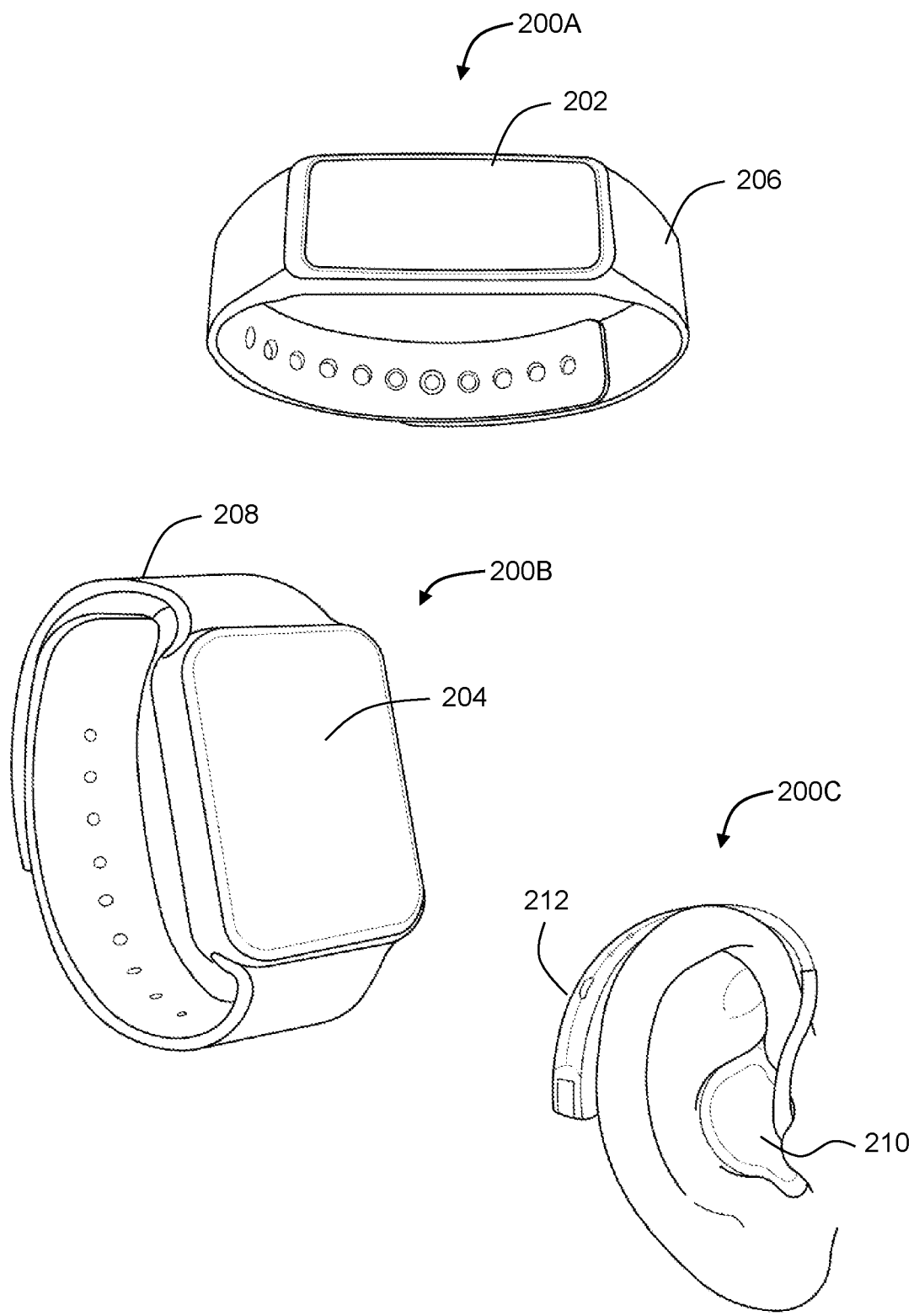
FIG. 2 illustrates various example implementations of a wearable electronic device included in the environment of FIG. 1.

FIG. 2 illustrates various example implementations 200A-200C of the wearable electronic device 104 of FIG. 1, arranged in accordance with at least one embodiment described herein. For instance, and with combined reference to FIGS. 1 and 2, the wearable electronic device 104 of FIG. 1 may be implemented as a fitness tracker 200A, a smartwatch 200B, or a hearing aid 200C.

The fitness tracker 200A and the smartwatch 200B may typically be worn on a wrist of the user 102 but may alternatively or additionally be worn elsewhere on an arm or leg of the user 102. Each of the fitness tracker 200A and the smartwatch 200B may include an electronics package 202 or 204 with one or more of the sensors described herein integrated therein and located at or near a back side of the electronics package 202 or 204 to be in contact or near contact with the skin of the user 102.

Each of the fitness tracker 200A and the smartwatch 200B additionally includes a watchband 206 or 208. Some fitness trackers, smartwatches, and regular watches (e.g., non-smartwatches) have removable watchbands. Embodiments described herein include wearable electronic devices 104 implemented as watchbands in which one or more of the sensors described herein may be integrated therein at or near an inside surface of the watchband. Thus, legacy fitness trackers, smartwatches, and/or regular watches (e.g., devices that lack the sensors described herein to detect medication adherence) can in some embodiments be retrofitted with a watchband that includes one or more of the sensors described herein to thereby detect medication adherence.

The hearing aid 200C may include at least an inner portion 210 that extends at least partially into an ear canal of the user 102 when in use. The hearing aid 200C may additionally include an outer portion 210 located external to the ear canal of the user 102 when in use. One or more of the sensors described herein may be integrated into the inner portion 210 to be in contact or near contact with skin in the ear canal of the user 102. Alternatively or additionally, one or more of the sensors described herein may be integrated into the outer portion 212 to be in contact or near contact with skin of the user's outer ear and/or with skin of the user's head.

In some embodiments, a single given user may simultaneously use two or more wearable electronic devices as described herein, each located at a different location on the user's body. Information generated by the sensors of the wearable electronic devices may be collected at one of the wearable electronic devices and/or at a smartphone, a PC, the remote server 110 of FIG. 1, or other computer device and may be time synchronized to work together.

FIG. 2 illustrates only three example implementations of the wearable electronic device 104 of FIG. 1. In still other embodiments, the wearable electronic device 104 of FIG. 1 may be implemented as a clip-on ear ring or other clip-on ear accessory, a gauged earring, an earring with a pin for pierced ears, eye glasses (e.g., with sensors in nose piece, ear stems, or other location in contact with skin of user), a watchband, a dermal patch, an armband, a finger ring, a necklace, footwear (e.g., with sensors in insoles or uppers of shoes, sandals, or other footwear), or other suitable form factor that in at least some embodiments positions corresponding sensors in contact with skin of the user. Depending on the form factor, detection of sweat vapor and/or markers in the sweat vapor may be detected in sweat vapor excreted as sweat from skin of the user at the user's ear lobe, ear canal, outer ear, behind the ear, temple, nose, front/back/side of neck or chest, palm of foot, wrist, finger, upper arm, lower arm, upper leg, lower leg, stomach, back, or virtually any other location of the user's skin.

Returning to FIG. 1, the wearable electronic device 104 may include a user interface to output data to the user 102 and/or to receive input data from the user. The user interface of the wearable electronic device 104 may include at least one of a microphone, a speaker, a display, a touchscreen display, an accelerometer, a button, or other suitable input/output device(s). The wearable electronic device 104 may use the user interface e.g., to output reminders from a digital calendar or calendar app or the like to the user 102 to take a corresponding one of the therapeutic agents 114, to query the user 102 regarding whether the user 102 has taken the corresponding therapeutic agent 114 and receive input in response thereto, to query the user to provide a self-assessment of the condition being treated by the corresponding therapeutic agent 114 and receive input in response thereto, or to output other data to or receive other data from the user 102.

The remote server 110 may include a collection of computing resources available in the cloud 108. The remote server 110 may be configured to receive measurements, determinations, calculations, user input, or other information from the wearable electronic device 104, the smartphone 106, a PC dongle, an TOT appliance, or other device in the environment 100.

Figure 3:
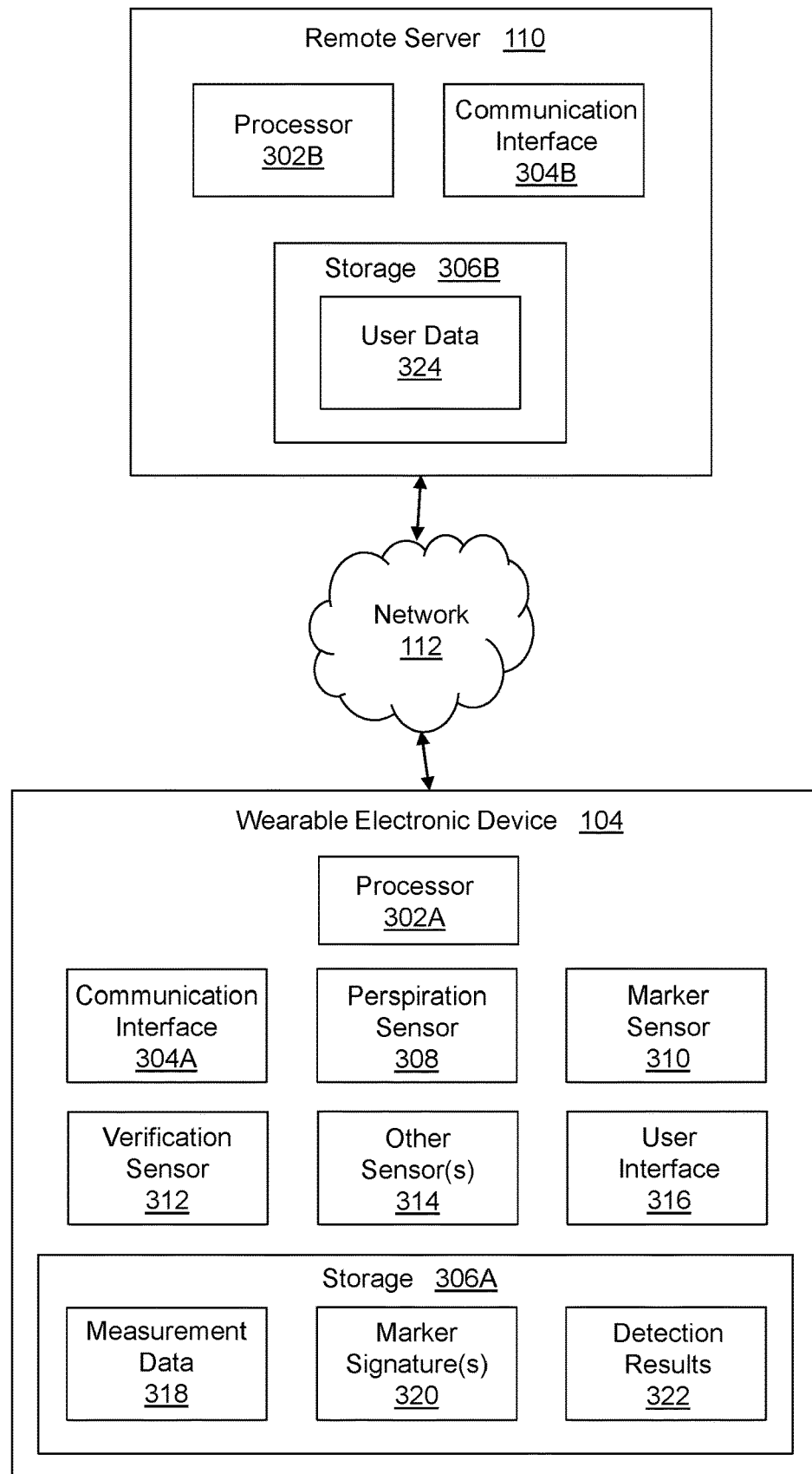
FIG. 3 is a block diagram of the wearable electronic device and a remote server of FIG. 1.

FIG. 3 is a block diagram of the wearable electronic device 104 and remote server 110 of FIG. 1, arranged in accordance with at least one embodiment described herein. Each of the wearable electronic device 104 and the remote server 110 may include a processor 302A or 302B (generically "processor 302" or "processors 302"), a communication interface 304A or 304B (generically "communication interface 304" or "communication interfaces 304"), and a storage and/or memory 306A or 306B (generically "storage 306"). Although not illustrated in FIG. 3, the smartphone 106 of FIG. 1 may be configured in a similar manner as the wearable electronic device 104 as illustrated in FIG. 3. For instance, the smartphone 106 may include the same, similar, and/or analogous elements or components as illustrated in FIG. 3.

Each of the processors 302 may include an arithmetic logic unit, a microprocessor, a general-purpose controller, or some other processor or array of processors, to perform or control performance of operations as described herein. The processors 302 may be configured to process data signals and may include various computing architectures including a complex instruction set computer (CISC) architecture, a reduced instruction set computer (RISC) architecture, or an architecture implementing a combination of instruction sets. Although each of the wearable electronic device 104 and the remote server 110 of FIG. 3 includes a single processor 302, multiple processor devices may be included and other processors and physical configurations may be possible. The processor 302 may be configured to process any suitable number format including, but not limited to two's compliment numbers, integers, fixed binary point numbers, and/or floating point numbers, all of which may be signed or unsigned.

Each of the communication interfaces 304 may be configured to transmit and receive data to and from other devices and/or servers through a network bus, such as an $I^2C$ serial computer bus, a universal asynchronous receiver/transmitter (UART) based bus, or any other suitable bus. In some implementations, each of the communication interfaces 304 may include a wireless transceiver for exchanging data with other devices or other communication channels using one or more wireless communication methods, including IEEE 802.11, IEEE 802.16, BLUETOOTH®, Wi-Fi, Zigbee, near field communication (NFC), or another suitable wireless communication method.

The storage 306 may include a non-transitory storage medium that stores instructions or data that may be executed or operated on by a corresponding one of the processors 302. The instructions or data may include programming code that may be executed by a corresponding one of the processors 302 to perform or control performance of the operations described herein. The storage 306 may include a non-volatile memory or similar permanent storage media including a flash memory device, an electrically erasable and programmable read only memory (EEPROM), a magnetic memory device, an optical memory device, or some other mass storage for storing information on a more permanent basis. In some embodiments, the storage 306 may also include volatile memory, such as a dynamic random access memory (DRAM) device, a static random access memory (SRAM) device, or the like.

The wearable electronic device 104 may additionally include at least a chemical marker sensor 310 ("Marker Sensor 310" in FIG. 3) and a verification sensor 312. Optionally, the wearable electronic device 104 may further include a perspiration sensor 308, one or more other sensors 314, and a user interface 316.

The perspiration sensor 308 may be configured to detect sweat vapor of a user. In some embodiments, the perspiration sensor 208 may detect or measure a quantity of sweat vapor. Examples of suitable perspiration sensors 308 are marketed by SENSIRION, ST, and BOSCH as humidity and temperature sensors and may include SENSIRION'S SHT31 SENSOR, ST'S HTS221 SENSOR, or BOSCH'S BME280 sensor.

The chemical marker sensor 310 may be configured to detect one or more markers in the sweat vapor. The chemical marker sensor 310 may be tuned to a particular marker or may be configured to detect multiple distinct markers. Alternatively or additionally, the chemical marker sensor 310 may be configure detect a quantity, proportion, and/or concentration of one or more markers. In some embodiments, the chemical marker sensor 310 includes a vapor permeable and liquid impermeable membrane to allow sweat vapor to enter into a sensing volume while keeping liquid sweat and/or other potential contaminants out of the sensing volume. The chemical marker sensor 310 may include at least one of a hot plate detector (an example of which is marketed by BOSCH as BOSCH's BME680 sensor), a metal-oxide gas sensor (an example of which is marketed by SENSIRION as SENSIRION's SGPC10 sensor), a graphene nanoelectronic heterodyne sensor, an infrared sensor (e.g., a mid-infrared sensor), or a capacitive micromachined ultrasonic transducer (CMUT)-based chemical sensor. Examples of some of the foregoing are disclosed in the following references which are incorporated herein by reference: (1) Kulkarni, G. S. et al. Graphene nanoelectronic heterodyne sensor for rapid and sensitive vapour detection. Nat. Commun. 5:4376 doi: 10.1038/ncomms5376, (2) U.S. Pat. No. 9,046,650, (3) Lee, H. J., et al. Highly Sensitive Detection of DMMP Using a CMUT-based Chemical Sensor, available at http://stanford.edu/group/khuri-yakub/publications/10_Lee_01.pdf (accessed on Nov. 15, 2016), and (4) Gardner, J. S. et al. CMOS Interfacing for Integrated Gas Sensors: A Review. IEEE Sensors Journal, Vol. 10, No. 12, December 2010.

In some embodiments, the chemical marker sensor 310 may include or be replaced by a sensor that measures a manifestation of a chemical reaction that involves the one or more markers. For instance, niacin (nicotinic acid) is a GRAS compound and causes skin flush. Rather than directly detecting the niacin, a sensor such as a camera or other image or optical sensor could detect a color shift at the surface of the skin, which color shift may be caused by a chemical reaction involving the niacin, to detect the niacin. Thus embodiments described herein may determine whether one or more markers are included in a therapeutic agent by, e.g., detecting a manifestation of a chemical reaction that involves the one or more markers and/or by detecting a compound that a marker may be transformed into without directly detecting the marker.

The verification sensor 312 may be configured to detect whether the wearable electronic device 104 is in use. In some embodiments, this may be accomplished by detecting whether the wearable electronic device 140 as a whole, the perspiration sensor 308, the marker sensor 310, and/or the verification sensor 312 is less than a threshold distance from skin (e.g., of the user 102) using an infrared sensor or other suitable sensor as the verification sensor 312. Alternatively or additionally, particular movement patterns detectable by an accelerometer and/or gyroscopic sensor as the verification sensor 312 may indicate whether the wearable electronic device 104 is in use. Thus, the verification sensor 312 may include at least one of an infrared sensor, an accelerometer, or a gyroscopic sensor. Alternatively or additionally, the verification sensor 312 may include at least one of a camera or other image sensor, a microphone or other audio sensor, or other suitable sensor to verify when the wearable electronic device is in use. One or more of the foregoing sensors used as the verification sensor 312 may alternatively or additionally be used as a biometric authentication sensor.

Accordingly, the one or more other sensors 314 may include at least one biometric authentication sensor configured to biometrically authenticate an identity of the user that is using the wearable electronic device 104. The biometric authentication sensor may include at least one of an accelerometer, a fingerprint scanner, a microphone, an image sensor, an ECG sensor, a PPG sensor, or other sensor suitable to generate signals that include or from which can be derived biometric characteristics of the user, referred to as user-specific biometric characteristics. The user-specific biometric characteristics can be compared to biometric characteristics of a particular known person, referred to as person-specific biometric characteristics. The particular known person may be associated with the wearable electronic device 104 and may have the person-specific biometric characteristics generated and stored on in the storage 306A for subsequent biometric authentication. The particular known person may also have, e.g., a prescription for a particular therapeutic agent. Embodiments described herein allow detection of medication adherence by a user and/or authentication of the user as the particular known person to track medication adherence of the particular known person.

The one or more other sensors 314 may alternatively or additionally include a sensor configured to detect manifestations of an expected effect of a therapeutic agent. For instance, if the user has arthritis and the therapeutic agent is intended to reduce inflammation, pain, and/or stiffness associated with arthritis, the one or more sensors 314 may include an accelerometer, a gyroscopic sensor, or other sensor that detects movement or motion of the user. Pain, inflammation, and/or stiffness may affect movement or motion patterns of the user. Thus, an expected effect of the therapeutic agent may be a reduction in pain, inflammation, and/or stiffness, which may manifest as a change in the movement pattern of the user from a first movement pattern indicative of a first level of pain, inflammation, and/or stiffness to a second movement pattern indicative of a second level of pain, inflammation, and/or stiffness that is lower than the first level. Other expected effects may manifest in the user's body in other ways that may be detected using other sensors, such as ECG sensors, PPG sensors, microphones or other audio sensors, and/or other sensors.

The user interface 316 may be similar or identical to the user interface described above with respect to FIG. 1. In particular, the user interface 316 may be configured to output data to the user and/or to receive input data from the user. The user interface 316 may include at least one of a microphone, a speaker, a display, a touchscreen display, an accelerometer, a button, or other suitable input/output device(s). The user interface 316 may be configured e.g., to output reminders from a digital calendar or calendar app or the like to the user to take a therapeutic agent, to query the user regarding whether the user has taken the therapeutic agent and receive input in response thereto, to query the user to provide a self-assessment of the condition being treated by the corresponding therapeutic agent and receive input in response thereto, or to output other data to or receive other data from the user.

The storage 306A may include measurement data 318, one or more marker signatures 320, and/or detection results 322. The measurement data may include measurements from one or more of the sensors 308, 310, 312, 314 and/or information derived therefrom. The marker signatures 320 may include data that associates unique markers, unique combinations of markers, and/or unique proportions or concentrations thereof with particular therapeutic agents and/or sources thereof. Thus, a particular marker, a particular combination of multiple markers, and/or a particular combination and proportions/concentrations of multiple markers that are detected together form a marker signature that can be looked up in the marker signatures 320 to identify a corresponding therapeutic agent and/or a source thereof. Such a marker scheme may allow authentication of therapeutic agents, e.g., as being from an authorized or otherwise known source.

Some embodiments of the marker signatures as described herein may allow for multiple "levels" of identification, analogous to multi-level NAND memory cells. In a single level scheme, each detectable marker may be analogous to a single level cell that can be either on (e.g., detected) or off (e.g., not detected). If there are n detectable markers, a total of $2^n$ unique combinations of markers (or marker signatures) are possible. In a multi-level scheme, each of the n detectable markers may have one of m possible proportions or concentrations (e.g., $\{1, 2, 3, 4\}$ or $\{1, 2, 4, 8\}$ or $\{1, 3, 5, 7\}$ for m=2; that is, m=log 2(elements)) in its on state, leading to a total of $2^{n*m}$ unique combinations of markers and proportions (or marker signatures).

The detection results 322 may include information identifying markers, marker signatures, and/or corresponding therapeutic agents detected by the wearable electronic device 104. Alternatively or additionally, the detection results 322 may include a confidence level calculated for markers, marker signatures, and/or corresponding therapeutic agents detected by the wearable electronic device 104. Alternatively or additionally, the detection results 322 may include a detection time or other information of each of the markers, marker signatures, and/or corresponding therapeutic agents detected by the wearable electronic device 104.

Referring to the remote server 110, it may include user data 324 and/or other data stored in the storage 306B. The user data 324 may include measurement data, detection results, input date, and/or other data received from wearable electronic devices of multiple users. In some embodiments, the wearable electronic device 104 may provide measurement data 318 to the remote server 110 which may process the measurement data 318 to detect medication adherence remotely from the wearable electronic device 104. Alternatively or additionally, the remote server 110 may perform more robust or additional or different processing on some or all of the user data 324 than is performed at the wearable electronic device 104. For instance, wearable electronic device 104 may make an initial determination about whether the user has taken a therapeutic agent based only on measurement data 318 from the chemical marker sensor 310, the verification sensor 312, and optionally the perspiration sensor 308. In comparison, the remote server 110 may make a final or at least more robust or more involved determination about whether the user has taken the therapeutic agent based on some or all of the foregoing as well as based on subjective input from the user (e.g., subjective input from the user indicating whether the user has taken the therapeutic agent and/or subjective input from the user indicating a self-assessment by the user of a condition being treated by the therapeutic agent), calendar information, objective measurement data indicative of whether an expected effect of the therapeutic agent is manifest in the user, and/or other information. Alternatively, all of the processing may be performed locally at the wearable electronic device 104.

Figure 4:
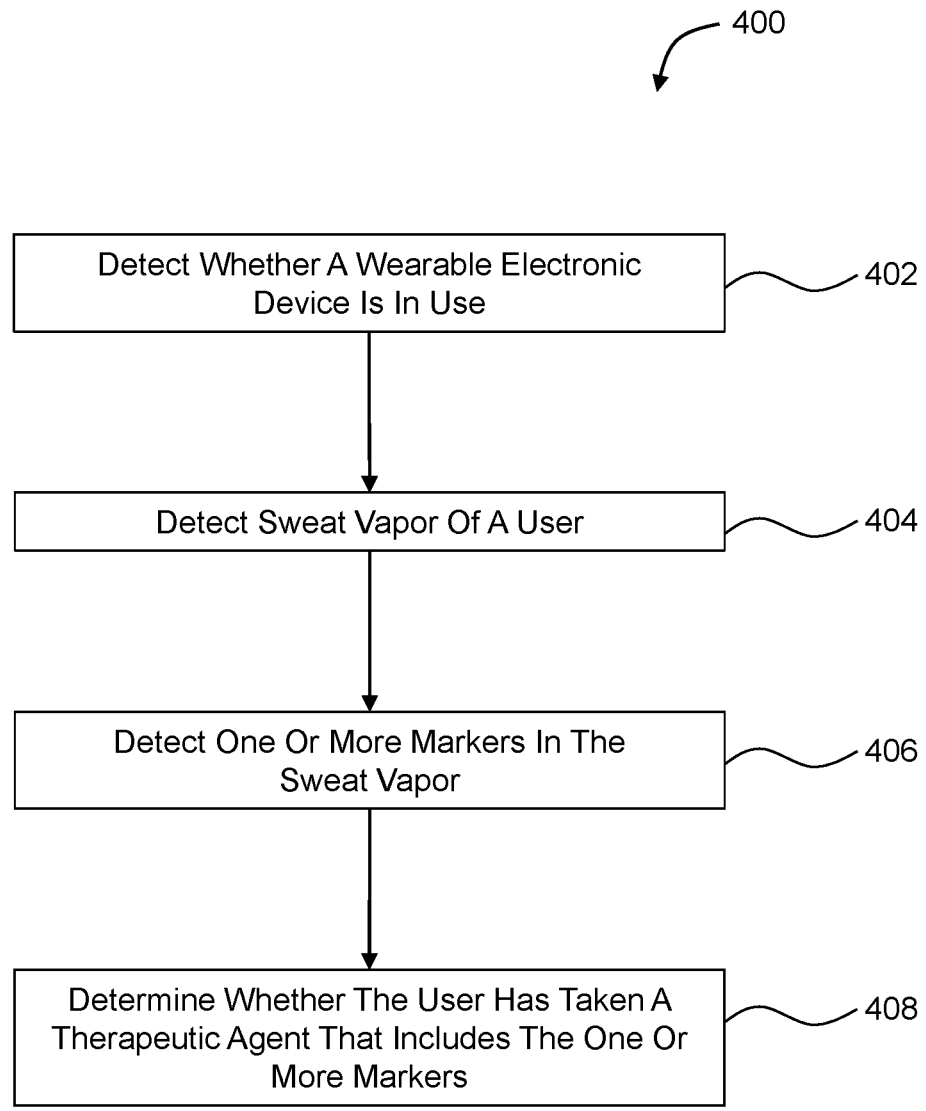
FIG. 4 includes a flow chart of an example method to determine medication adherence, all arranged in accordance with at least one embodiment described herein.

FIG. 4 is a flowchart of an example method 400 to determine medication adherence, arranged in accordance with at least one embodiment described herein. The method 400 may be implemented, in whole or in part, by the wearable electronic device 104, the smartphone 106, and/or the remote server 110 described elsewhere herein. Alternatively or additionally, software in the form of computer-executable instructions stored in one or both of the storage 306A or 306B of FIG. 3 may be executed by one or both of the processor 302A or 302B to cause the corresponding processor 302A and/or 302B to perform or control performance of one or more of the operations or blocks of the method 400. The method 400 may include one or more of blocks 402, 404, 406, and/or 408. The method 400 may begin at block 402.

At block 402, it may be detected whether a wearable electronic device is in use. Detecting whether the wearable electronic device is in use may include the verification sensor 312 of FIG. 3 detecting whether the wearable electronic device 104 is in use. For instance, detecting whether the wearable electronic device is in use may include detecting whether the perspiration sensor 308, the chemical marker sensor 310 and/or the verification sensor 312 is less than a threshold distance from skin using an infrared sensor. Block 402 may be followed by block 404.

At block 404, sweat vapor of a user may be detected using a perspiration sensor of the wearable electronic device. Detecting the sweat vapor of the user may include detecting a quantity, volume, or other measurement of the sweat vapor of the user using, e.g., the perspiration sensor 308 of FIG. 3. Alternatively or additionally, detecting the sweat vapor of the user may include detecting the sweat vapor from at least one of: a wrist of the user, an ear canal of the user, or an ear lobe of the user. In other embodiments, sweat vapor may not be detected such that block 404 may be omitted. Block 404, or block 402 if block 404 is omitted, may be followed by block 406.

At block 406, one or more markers in the sweat vapor may be detected using a chemical marker sensor of the wearable electronic device. Detecting the one or more markers in the sweat vapor may include detecting the one or more markers using the chemical marker sensor 310 of FIG. 3. The specific markers and/or their proportions or concentrations that are detected by the chemical marker sensor may depend on the particular therapeutic agent taken by the user and the specific markers and/or their proportions or concentrations contained therein such that detection of the specific markers and/or their proportions or concentrations may be used to determine that the user has taken the particular therapeutic agent. Block 406 may be followed by block 408.

At block 408, and in response to detecting that the system is in use, it is determined whether the user has taken a therapeutic agent that includes the one or more markers based on detecting both the sweat vapor and the one or more markers in the sweat vapor. In some embodiments, determining whether the user has taken the therapeutic agent includes calculating a confidence level that the user has taken the therapeutic agent based on detecting both the sweat vapor and the one or more markers in the sweat vapor and based on at least one of: objective measurement data indicative of whether an expected effect of the therapeutic agent is manifest in the user; subjective first input data from the user that indicates whether the user has taken the therapeutic agent; subjective second input data from the user that indicates a self-assessment by the user of a condition being treated by the therapeutic agent; or calendar information indicative of any reminders related to the user taking the therapeutic agent.

In some embodiments, detecting the one or more markers in the sweat vapor at block 406 includes detecting multiple markers in the sweat vapor. In these and other embodiments, the method 400 may further include identifying a given specific therapeutic agent taken by the user based on both a proportion and identity of each of the multiple markers that are detected in the sweat vapor, where the proportion and identity of the multiple markers may be unique to the given specific therapeutic agent, e.g., as a marker signature.

Alternatively or additionally, detecting the one or more markers in the sweat vapor at block 406 may include detecting at least two markers of different metabolic rates in the sweat vapor of the user. Detecting the at least two markers may include detecting a first one of the at least two markers at a first time and detecting at least a second one of the at least two markers at a second time subsequent to the first time. Detection of the first one of the at least two markers at the first may indicate that the user has taken the therapeutic agent. Detection of the at least the second one of the at least two markers at the second time relative to the first time may indicate a metabolic rate of the user. In some embodiments, the method 400 may further include determining a metabolic rate of the user based on the first time, the second time, or a difference between the two. By determining the metabolic rate and/or the difference in time between detecting the first marker and the second marker, how quickly the therapeutic agent is metabolized by the user may be determined as an input in personalizing dosing for the user.

In some embodiments, the method 400 may further include biometrically authenticating the user as a particular known person. In these and other embodiments, biometrically authenticating the user as the particular known person may include determining user-specific biometric characteristics of the user, comparing the user-specific biometric characteristics to person-specific biometric characteristics of the particular known person, and determining that the user is the particular known person in response to the user-specific biometric characteristics matching the person-specific biometric characteristics. The user-specific biometric characteristics may include at least one of user-specific gait characteristics, user-specific fingerprint characteristics, user-specific voice characteristics, user-specific image characteristics, or user-specific heart beat characteristics. The person-specific biometric characteristics may include at least one of person-specific gait characteristics, person-specific fingerprint characteristics, person-specific voice characteristics, person-specific image characteristics, or person-specific heart beat characteristics.

In some embodiments, the method 400 may further include authenticating a source and/or identity of the therapeutic agent. In these and other embodiments, marker signatures may be used similar to barcodes to uniquely identify a source (e.g., a particular pharmaceutical company) and/or identity of a therapeutic agent. Thus, authenticating the source and/or the identity of the therapeutic agent may include determining a marker signature of the therapeutic agent, comparing the determined marker signature to a unique known marker signature associated with a known source and/or identity of a known therapeutic agent, and determining that the source of the therapeutic agent is the known source of the known therapeutic agent in response to the marker signature of the therapeutic agent matching the known marker signature. Determining the marker signature of the therapeutic agent may include identifying at least two different markers in the sweat vapor and determining a concentration of each of the at least two different markers.

Alternatively or additionally, the method 400 may further include determining a baseline measurement of the one or more markers in the sweat vapor of the user during a baseline period of time prior to the user taking the therapeutic agent. In these and other embodiments, detecting the one or more markers in the sweat vapor may include determining a subsequent measurement of the one or more markers in the sweat vapor of the user subsequent to the baseline period of time. The method 400 may further include comparing the subsequent measurement to the baseline measurement. Determining whether the user has taken the therapeutic agent may include determining that the user has taken the therapeutic agent in response to the subsequent measurement exceeding the baseline measurement by a threshold amount.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Some embodiments described herein have generally been described as processing information generated by sensors and/or information derived therefrom at a wearable electronic device to determine medication adherence and/or to detect counterfeit drugs. Alternatively or additionally, the information generated by the sensors and/or information derived therefrom may be processed exclusively at a smartphone such as the smartphone 106 of FIG. 1, at a remote server such as the remote server 110 of FIG. 1, or at another computer device to determine medication adherence and/or to detect counterfeit drugs. Alternatively or additionally, the information generated by the sensors and/or information derived therefrom may be processed at two or more of a wearable electronic device, a smartphone, a remote server, or other computer device to determine medication adherence and/or to detect counterfeit drugs.

Embodiments disclosed herein have generally been described in the context of determining medication adherence. Alternatively or additionally, embodiments described herein may be implemented in counterfeit drug detection. For instance, some generic drugs on international markets may copy name brand drugs that may have patents in one or more jurisdictions in terms of, e.g., packaging, branding, etc. Pharmaceutical companies and/or other entities may use wearable electronic devices as described herein together with user segmentation (e.g., Geography—isolating counterfeit distributors in a region or geography, and Payer Mapping—counterfeit sourcing per pharmaceutical distributor) to then flag groups or individuals who claim to be taking the name brand drug and are wearing such wearable electronic devices as taking counterfeit drugs where the wearable electronic devices do not detect one or more markers that the pharmaceutical companies or other entities know are in the name brand drug.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A system to determine medication adherence, the system comprising:
   a chemical marker sensor configured to detect one or more markers of a therapeutic agent in sweat vapor of a user;
   a verification sensor configured to detect whether the system is less than a threshold distance from skin;
   a heart-beat sensor configured to detect a manifestation of an expected effect of the therapeutic agent on the user; and
   a processor communicatively coupled to the chemical marker sensor, the verification sensor, and the heart-beat sensor, and configured to calculate a confidence level indicative of whether the user has taken the therapeutic agent based on the chemical marker sensor detecting the one or more markers in the sweat vapor, the verification sensor detecting that the system is less than the threshold distance from skin, and the heart-beat sensor detecting the manifestation of the expected effect of the therapeutic agent on the user.

2. The system of claim 1, wherein:
   the chemical marker sensor is configured to detect a plurality of markers in the sweat vapor; and
   the processor is configured to identify specific therapeutic agents taken by the user based on, for a given specific therapeutic agent, at least one of a proportion or an identity of each of two or more markers of the plurality of markers that are detected in the sweat vapor and that are specific to the given specific therapeutic agent.

3. The system of claim 1, further comprising a wristband, a wristwatch, or a smartwatch that includes at least a perspiration sensor configured to detect the sweat vapor of the user, the chemical marker sensor, and the verification sensor and configured to position the perspiration sensor to detect sweat vapor from a wrist of the user.

4. The system of claim 1, further comprising a hearing aid that includes at least a perspiration sensor configured to detect the sweat vapor of the user, the chemical marker sensor, and the verification sensor and configured to position the perspiration sensor to detect sweat vapor from an ear canal of the user.

5. The system of claim 1, further comprising a clip-on ear accessory that includes at least a perspiration sensor configured to detect the sweat vapor of the user, the chemical marker sensor, and the verification sensor and configured to position the perspiration sensor to detect sweat vapor from an ear lobe of the user.

6. The system of claim 1, wherein the chemical marker sensor comprises at least one of a hot plate detector, a metal-oxide gas sensor, a graphene nanoelectric heterodyne sensor, an infrared sensor, or a capacitive micromachined ultrasonic transducer (CMUT)-based chemical sensor.

7. The system of claim 1, further comprising at least one biometric authentication sensor configured to biometrically authenticate the user as a particular known person.

8. The system of claim 7, wherein the at least one biometric authentication sensor comprises at least one of an accelerometer, a fingerprint scanner, a microphone, an image sensor, an electrocardiograph (ECG) sensor, or a photoplethysmograph (PPG) sensor.

9. The system of claim 1, wherein the verification sensor comprises an infrared sensor or an accelerometer.

10. A system to determine medication adherence, the system comprising:
    a chemical marker sensor configured to detect one or more markers of a therapeutic agent in sweat vapor of a user;
    a verification sensor configured to detect whether the system is less than a threshold distance from skin;
    at least one of a heart-beat sensor or a motion sensor, the at least one of the heart-beat sensor or the motion sensor configured to detect a manifestation of an expected effect of the therapeutic agent on the user; and
    a processor communicatively coupled to the chemical marker sensor, the verification sensor, and the at least one of the heart-beat sensor or the motion sensor and configured to calculate a confidence level indicative of whether the user has taken the therapeutic agent based on the chemical marker sensor detecting the one or more markers in the sweat vapor, the verification sensor detecting that the system is less than the threshold distance from skin, and the at least one of the heart-beat sensor or the motion sensor detecting the manifestation of the expected effect of the therapeutic agent on the user.

11. A system to determine medication adherence, the system comprising:
    a chemical marker sensor configured to detect one or more markers of a therapeutic agent in sweat vapor of a user;
    a verification sensor configured to detect whether the system is less than a threshold distance from skin;
    a motion sensor configured to detect a change in a movement pattern of the user indicative of a manifestation of an expected effect of the therapeutic agent on the user;
    and
    a processor communicatively coupled to the chemical marker sensor, the verification sensor, the motion sensor, and the user interface and configured to calculate a confidence level indicative of whether the user has taken the therapeutic agent based on the chemical marker sensor detecting the one or more markers in the sweat vapor, the verification sensor detecting that the system is less than the threshold distance from skin, and the motion sensor detecting the change in the movement pattern of the user indicative of the manifestation of the expected effect of the therapeutic agent on the user.

12. The system of claim 10, wherein:
the one or more markers of the therapeutic agent include a first chemical marker and a second chemical marker;
the chemical marker sensor is configured to:
  detect the first chemical marker of the therapeutic agent in the sweat vapor at a first time; and
  detect the second chemical marker of the therapeutic agent in the sweat vapor at a second time; and
the processor is further configured to:
  determine a metabolic rate of the user based on the first time and the second time; and
  determine a personalized dosing for the user based on the metabolic rate.

\* \* \* \* \*